(12) United States Patent
Umebayashi

(10) Patent No.: US 10,070,996 B2
(45) Date of Patent: Sep. 11, 2018

(54) METHOD FOR PRODUCING DISPOSABLE UNDERWEAR-TYPE DIAPER

(71) Applicant: ZUIKO CORPORATION, Settu-shi, Osaka (JP)

(72) Inventor: Toyoshi Umebayashi, Settu (JP)

(73) Assignee: ZUIKO CORPORATION, Settu-Shi, Osaka (JP)

( * ) Notice: Subject to any disclaimer, the term of this patent is extended or adjusted under 35 U.S.C. 154(b) by 936 days.

(21) Appl. No.: 14/401,746

(22) PCT Filed: Apr. 10, 2013

(86) PCT No.: PCT/JP2013/060796
§ 371 (c)(1),
(2) Date: Nov. 17, 2014

(87) PCT Pub. No.: WO2013/179779
PCT Pub. Date: Dec. 5, 2013

(65) Prior Publication Data
US 2015/0297417 A1 Oct. 22, 2015

(30) Foreign Application Priority Data
May 29, 2012 (JP) .................................. 2012-121583

(51) Int. Cl.
*A61F 13/15* (2006.01)
*A61F 13/496* (2006.01)
(Continued)

(52) U.S. Cl.
CPC .. *A61F 13/15756* (2013.01); *A61F 13/15699* (2013.01); *A61F 13/15723* (2013.01);
(Continued)

(58) Field of Classification Search
CPC .......... A61F 13/15585; A61F 13/15699; A61F 13/15756; A61F 2013/15813; A61F 13/5655; A61F 13/565; B32B 2555/02
See application file for complete search history.

(56) References Cited

U.S. PATENT DOCUMENTS 6,491,676 B1 12/2002 Suzuki et al.
8,235,964 B2 8/2012 Perneborn
(Continued)

FOREIGN PATENT DOCUMENTS

EP 1702598 A1 9/2006
EP 2057975 A1 5/2009
(Continued)

OTHER PUBLICATIONS

European Patent Office, "Search Report for EP 13797506.6," dated Dec. 8, 2015.
(Continued)

*Primary Examiner* — Peter S Vasat
(74) *Attorney, Agent, or Firm* — Manabu Kanesaka

(57) ABSTRACT

Fasteners folded in two are arranged on one main surface of a first continuous body so that ends of the fasteners are arranged on the outside of the one main surface. A second continuous body is laid over another main surface of the first continuous body in a state where one end is bent so as to be laid over the other main surface, and the first continuous body and second continuous body are bonded together to form a composite continuous body to which the one end of the fasteners is fixed. The composite continuous body is cut to form a piece on which the pair of fasteners is arranged only in a first region. The piece is folded in two along an imaginary line and overlapped, and then the other end of the fasteners is bent and laid over and fixed to a second region.

1 Claim, 5 Drawing Sheets

(51) Int. Cl.
*A61F 13/56* (2006.01)
*A61F 13/62* (2006.01)
*B32B 37/18* (2006.01)
*B32B 38/00* (2006.01)

(52) U.S. Cl.
CPC .. *A61F 13/15747* (2013.01); *A61F 13/15804* (2013.01); *A61F 13/496* (2013.01); *A61F 13/565* (2013.01); *A61F 13/5633* (2013.01); *A61F 13/622* (2013.01); *B32B 37/18* (2013.01); *B32B 38/0004* (2013.01); *B32B 38/0012* (2013.01); *B32B 2307/726* (2013.01); *B32B 2307/7265* (2013.01); *B32B 2555/02* (2013.01)

(56) References Cited

U.S. PATENT DOCUMENTS

| | | | |
|---|---|---|---|
| 8,287,512 | B2 | 10/2012 | Gabriele |
| 8,382,928 | B2* | 2/2013 | Umebayashi ..... A61F 13/15747 156/204 |
| 2002/0138062 | A1* | 9/2002 | Kuen ................. A61F 13/15699 604/386 |
| 2006/0241561 | A1 | 10/2006 | De Angelis |
| 2008/0082074 | A1* | 4/2008 | Soto .................. A61F 13/49011 604/385.26 |
| 2011/0100536 | A1 | 5/2011 | Umebayashi |
| 2011/0303351 | A1 | 12/2011 | Nakakado |

FOREIGN PATENT DOCUMENTS

| | | |
|---|---|---|
| JP | 3373611 B | 11/2002 |
| WO | 2007/123445 A1 | 11/2007 |

OTHER PUBLICATIONS

PCT, "International Search Report for International Application No. PCT/JP2013/060796".

* cited by examiner

Fig. 3
(a) 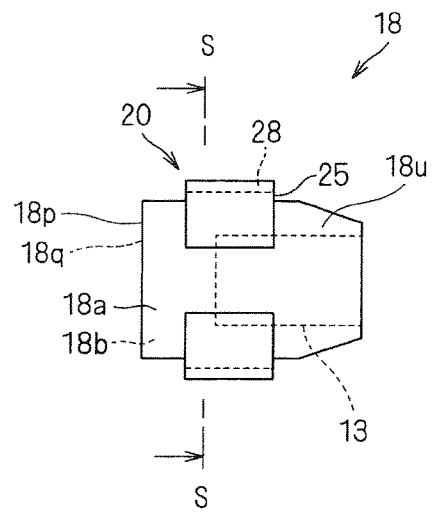
(b) 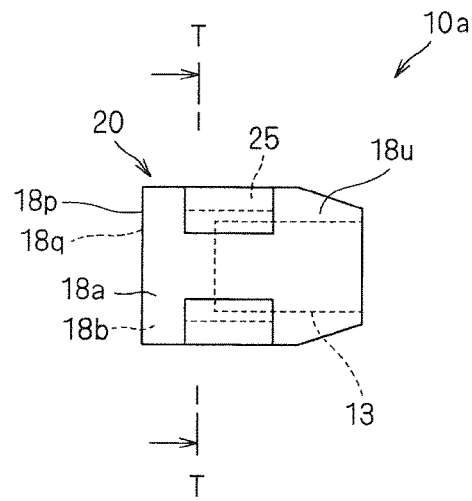
Fig. 4
(a) 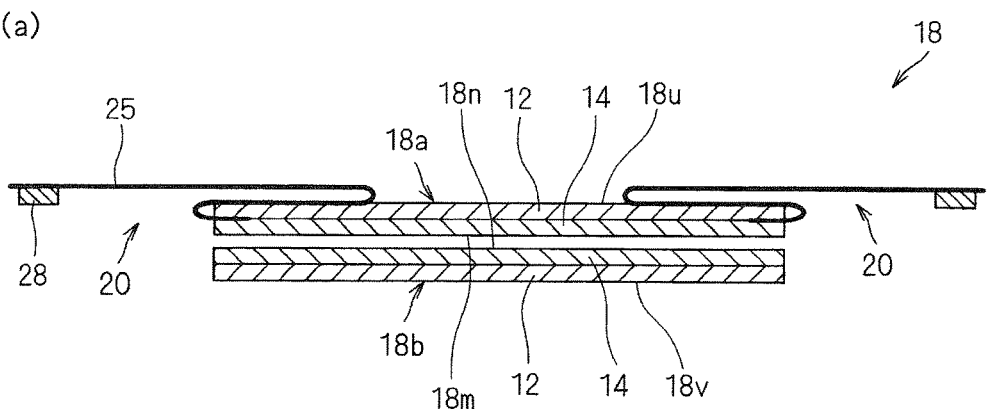
(b) 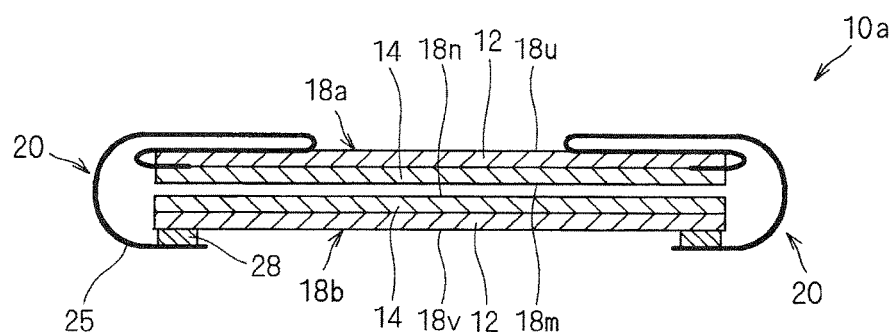

METHOD FOR PRODUCING DISPOSABLE UNDERWEAR-TYPE DIAPER

RELATED APPLICATIONS

The present application is National Phase of International Application No. PCT/JP2013/060796 filed Apr. 10, 2013, and claims priority from Japanese Application No. 2012-121583, filed May 29, 2012.

TECHNICAL FIELD

The present invention relates to a method for producing a disposable underwear-type diaper, and more specifically, to a method for producing a disposable underwear-type diaper having a fastener.

BACKGROUND ART

Conventionally, various types of so-called "underwear-type diapers" formed in a shape of briefs in advance have been proposed.

For example, FIG. 5 is a partially broken perspective view of a disposable underwear-type diaper 1. As shown in FIG. 5, the underwear-type diaper 1 is formed in an underwear shape where the upper parts of an abdomen side 8A and a back side 8B of a body 8 are connected by a pair of fasteners 40, and has a waist opening 5 and a pair of leg openings 6.

The body 8 includes a liquid transmitting top sheet 2 that is in contact with the skin of the wearer, a liquid non-transmitting back sheet 3, and an absorber 4 disposed between the top sheet 2 and the back sheet 3. The absorber 4 is disposed on the wearer's abdomen side and back side.

In the fastener 40, an abdomen side fastening piece 40A and a back side fastening pieces 40B are bonded together at a joint 41. The abdomen side fastening piece 40A includes a body 42 and a tape portion 43 where a tab 45 for nipping is formed. The tape portion 43 is detachably fixed to a target zone 44 fixed to the back sheet 3.

Since the disposable underwear-type diapers 1 are continuously produced, for example, by production steps schematically shown in FIG. 6, the abdomen side fastening piece 40A and the back side fastening pieces 40B are bonded together at the joint 41.

That is, as shown in FIG. 6, while a belt-like top sheet continuous body 52 for forming the top sheet 2 and a belt-like back sheet continuous body 53 for forming the back sheet 3 are conveyed in the directions of the lengths thereof as shown by the arrows, the absorber 4 conveyed in synchronism is disposed between the top sheet continuous body 52 and the back sheet continuous body 53, thereby forming a diaper web continuous body 51.

To the diaper web continuous body 51, fastening piece members 40A' and 40B' for forming the fastening pieces 40A and 40B are alternately fixed in the conveyance direction. Specifically, after a target zone member 44' for forming the target zone 44 is fixed to the surface of the back sheet continuous body 53, the tape portion 43 of the fastening piece member 40A' is pasted to the target zone member 44'. To a predetermined position of the top sheet continuous body 52, the fastening piece member 40B' is fixed.

Then, as shown at reference designation c, the diaper web continuous body 51 is cut in the direction of the width at a position where the fastening piece members 40A' and 40B' are divided in two, thereby forming a diaper web 50 to which the fastening pieces 40A and 40B are fixed.

Then, as shown at reference designation d, the diaper web 50 is folded in two along an imaginary line in a direction orthogonal to the direction of the flow thereof, and the side edges of the fastening pieces 40A and 40B facing each other are bonded together to form the joint 41.

PRIOR ART DOCUMENT

Patent Document

Patent Document 1: Japanese Patent Publication No. 3373611

SUMMARY OF THE INVENTION

Problem to be Solved by the Invention

When a fastener is formed by bonding two members together, a seam is formed on the fastener. Since the texture and softness are different between the neighborhood of the seam and other parts of the fastener, this can give a sense of discomfort to the wearer. It is desirable that the fastener be uniform in texture and softness by eliminating the seam in the middle portion.

However, when disposable underwear-type diapers are continuously produced, a joint is formed in the middle portion of the fastener.

In view of such circumstances, the present invention intends to provide a method for producing a disposable underwear-type diaper by which disposable underwear-type diapers provided with a fastener having no seam in a middle portion can be continuously produced.

Means for Solving the Problem

To solve the above-mentioned problem, the present invention provides a method for producing a disposable underwear-type diaper structured as follows:

A method for producing a disposable underwear-type diaper is provided with a first to fourth steps. (i) Sheet-like fasteners folded in two are arranged on one main surface of a belt-like first continuous body having a pair of side edges. At this time, the fasteners are arranged at intervals along the pair of side edges of the first continuous body so that a main surface of each fasteners is in contact with the one main surface, that both ends of the fasteners are disposed on the outside of the one main surface of the first continuous body when viewed from the direction of the normal to the one main surface and that a pair of the fasteners face each other in a direction in which the side edges of the first continuous body face each other. (ii) In the second step, a composite continuous body is formed by laying a belt-like second continuous body over an other main surface of the first continuous body in a state where one ends, on the first continuous body side, of the both ends of the fasteners are bent so as to be laid over the other main surface of the first continuous body so that the first continuous body and the second continuous body are bonded together and that the one ends of the fasteners are fixed. (iii) In the third step, the composite continuous body is cut to thereby form an individual piece divided by an imaginary line in two parts of a first region including the pair of fasteners facing each other and a second region not including the fasteners. (iv) In the fourth step, after the individual piece is folded in two along the imaginary line so that the first region and the second region are laid one over the other, the other ends of the fasteners are bent so as to be laid over the second region, and the other ends are fixed to the second region.

In the above-described method, the one ends of the fasteners are bent by the time the second continuous body is laid over the other main surface of the first main surface in the second step. The one ends of the fasteners may be bent when the fasteners are arranged on the one main surface of the first continuous body in the first step or therebefore.

Moreover, the one ends of the fasteners are fixed to some part of the composite continuous body during the period to when the composite continuous body is formed by the second step. For example, the one ends of the fasteners may be bent and fixed to the first continuous body after the fasteners are arranged on the one main surface of the first continuous body before the second continuous body is laid over the other main surface of the first continuous body in the second step. Alternatively, the one ends of the fasteners having already been bent may be fixed to the first continuous body and/or the second continuous body when the first and second continuous bodies are bonded together.

The first continuous body and the second continuous body are bonded together at the same time when the second continuous body is laid over the other main surface of the first continuous body, or thereafter by the time when the individual piece is formed.

The other end of the fastener may be bent halfway before the overlaying of the first region and the second region of the individual piece is completed. In that case, after the overlaying of the first region and the second region of the individual piece is completed, the other end of the fastener is completely bent and laid over the second region, and the other end of the fastener is fixed to the second region.

By the above-described method, the disposable underwear-type diapers can be continuously produced, for example, while the first continuous body and the second continuous body are being conveyed. The fastener can be made so that no seam is formed in the middle portion, for example, by forming it of one or more than one member that is continuous at least in the middle portion.

In the disposable underwear-type diaper produced by the above-described method, when the space between the first region and the second region of the individual piece folded in two is increased, a waist opening is formed between the cutting-plane lines of the individual piece, and a pair of leg openings are formed between the pair of fasteners and the imaginary line (bend line). By eliminating the seam in the middle portion between the one end and the other end of the fastener, the texture and softness can be made uniform.

When the individual piece is folded in two along the imaginary line so as to be laid one over the other in the above-described forth step, the middle portion of the fastener may be disposed on the outside of the individual piece.

Preferably, in the above-described fourth step, after the individual piece is folded in two along the imaginary line so that the fasteners are sandwiched between the first region and the second region, the other ends of the fasteners are bent to a side opposite to the one ends and laid over the second region, and the other ends are fixed to the second region.

In this case, the inner main surfaces, facing each other, of the first and second regions of the individual piece folded in two are formed of the one main surface of the first continuous body. When the individual piece is folded in two, the middle portion of the fastener is sandwiched between the first region and the second region of the individual piece. If the middle portion of the fastener is sandwiched between the first region and the second region of the individual piece, the handling of the individual piece thereafter is easy compared with a case where the middle portion of the fastener is disposed on the outside of the individual piece.

Specifically, the present invention may be carried out in various modes as follows:

In a preferred mode, the first continuous body includes a liquid transmitting top sheet forming the one main surface of the first continuous body. The second continuous body includes a liquid non-transmitting back sheet. In the second step, the first continuous body and the second continuous body are bonded together in a state where an absorber is disposed between the first continuous body and the second continuous body.

In this case, it may be performed to dispose the absorber on the first continuous body simultaneously with the first step, or before or after the first step and then, bond the first and second continuous bodies together. Or it may be performed to dispose the absorber on the second continuous body and then, bond the first and second continuous bodies together. Or it may be performed to dispose the absorber between the first and second continuous bodies immediately before the first and second continuous bodies are bonded together and then, bond the first and second continuous bodies.

In another preferred mode, the first continuous body includes a liquid transmitting top sheet forming the one main surface of the first continuous body, a liquid non-transmitting back sheet forming the other main surface of the first continuous body, and an absorber disposed between the top sheet and the back sheet. The second continuous body includes a liquid transmitting or liquid non-transmitting cover sheet.

In this case, in the first step, the absorber is disposed on the first continuous body.

Moreover, the present invention provides a disposable underwear-type diaper structured as follows:

The underwear-type diaper is provided with a body and a pair of fasteners. The body has a pair of end edges facing each other and a pair of side edges extending between the pair of end edges and facing each other. The body is divided into two parts of a first and second regions by an imaginary line extending between the pair of end edges, and folded in two along the imaginary line so that the first region and the second region are laid one over the other. The pair of fasteners are arranged along the pair of side edges at an interval from the imaginary line, one ends are fixed to the first region, and the other ends are fixed to the second region. When a space between the first and second regions is increased, a waist opening is formed between the end edges, and a pair of leg openings are formed between the pair of fasteners and the imaginary line. The body includes an inner member forming inner main surfaces, facing each other, of the first and second regions and an outer member forming outer main surfaces on the opposite side of the inner main surfaces of the first and second regions. In each of the fasteners, (a) the one end is fixed to the first region in a state of being disposed between the inner member and the outer member, (b) the other end is fixed to the outer main surface of the second region, and (c) a middle portion between the one end and the other end is continuous without a seam.

In the above-described structure, the one end of the fastener is fixed to the inner member and/or the outer member. Since no seam is formed in the middle portion of the fastener, a sense of discomfort is never given to the wearer by a seam in the middle portion. The disposable underwear-type diaper of the above-described structure can be continuously produced.

Advantage of the Invention

According to the present invention, a disposable underwear-type diaper provided with a fastener having no seam in the middle portion can be continuously produced.

BRIEF DESCRIPTION OF THE DRAWINGS

FIG. 3 Schematic views showing production steps (second embodiment).

FIG. 4 Schematic views of cross sections in the production steps (second embodiment).

MODE FOR CARRYING OUT THE INVENTION

Hereinafter, embodiments of the present invention will be described with reference to FIG. 1 to FIG. 4.

First Embodiment

A method for producing a disposable underwear-type diaper 10 of a first embodiment will be described with reference to FIG. 1 and FIG. 2.

Figure 1:
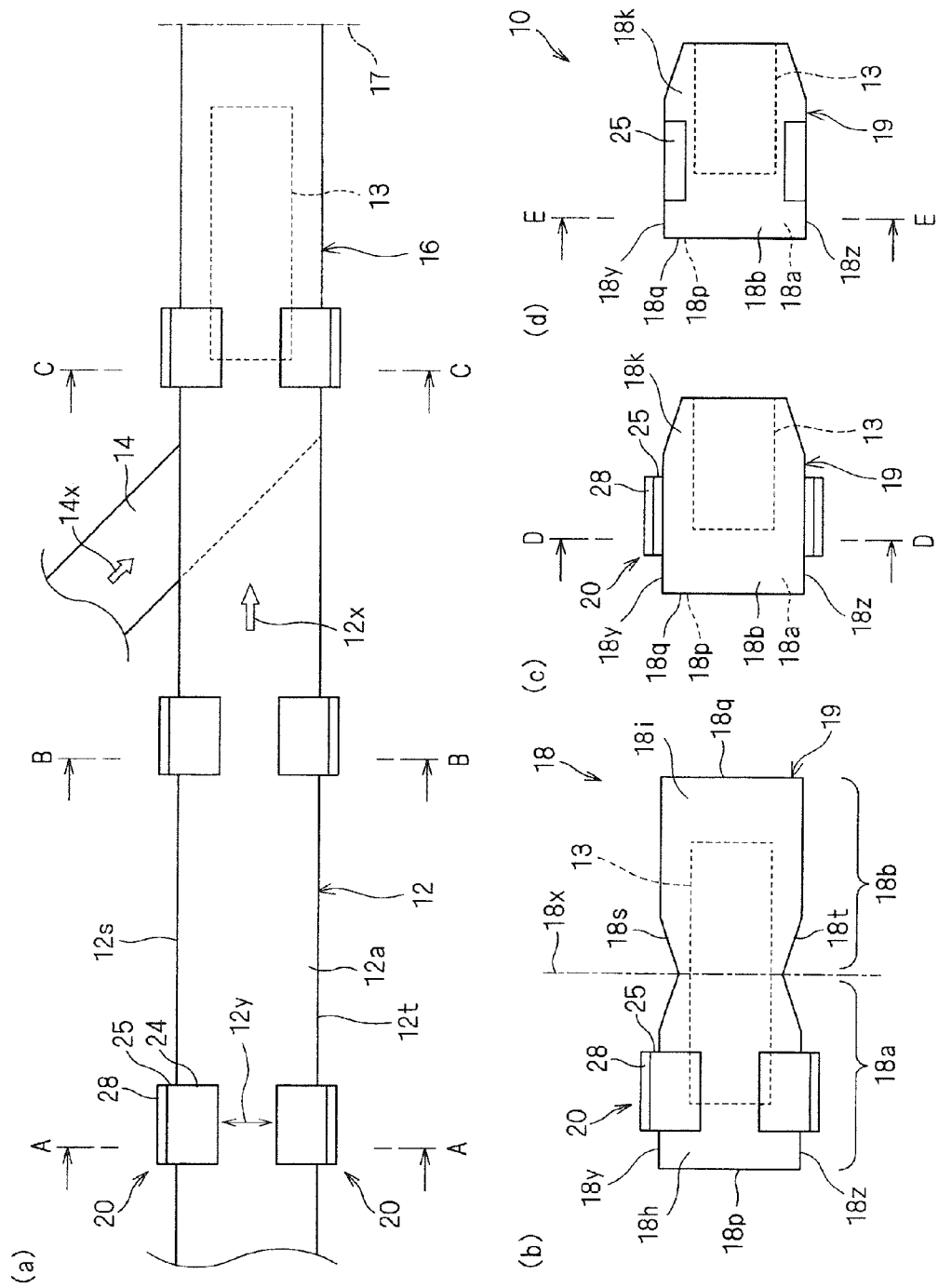
FIG. 1 Schematic views showing production steps (first embodiment).

FIGS. 1(*a*) to 1(*d*) are schematic views showing the method for producing the disposable underwear-type diaper 10. FIG. 2(*a*) is a schematic view of a cross section taken along line A-A of FIG. 1(*a*). FIG. 2(*b*) is a schematic view of a cross section taken along line B-B of FIG. 1(*a*). FIG. 2(*c*) is a schematic view of a cross section taken along line C-C of FIG. 1(*a*). FIG. 2(*d*) is a schematic view of a cross section taken along line D-D of FIG. 1(*c*). FIG. 2(*e*) is a schematic view of a cross section taken along line E-E of FIG. 1(*d*).

Figure 2:
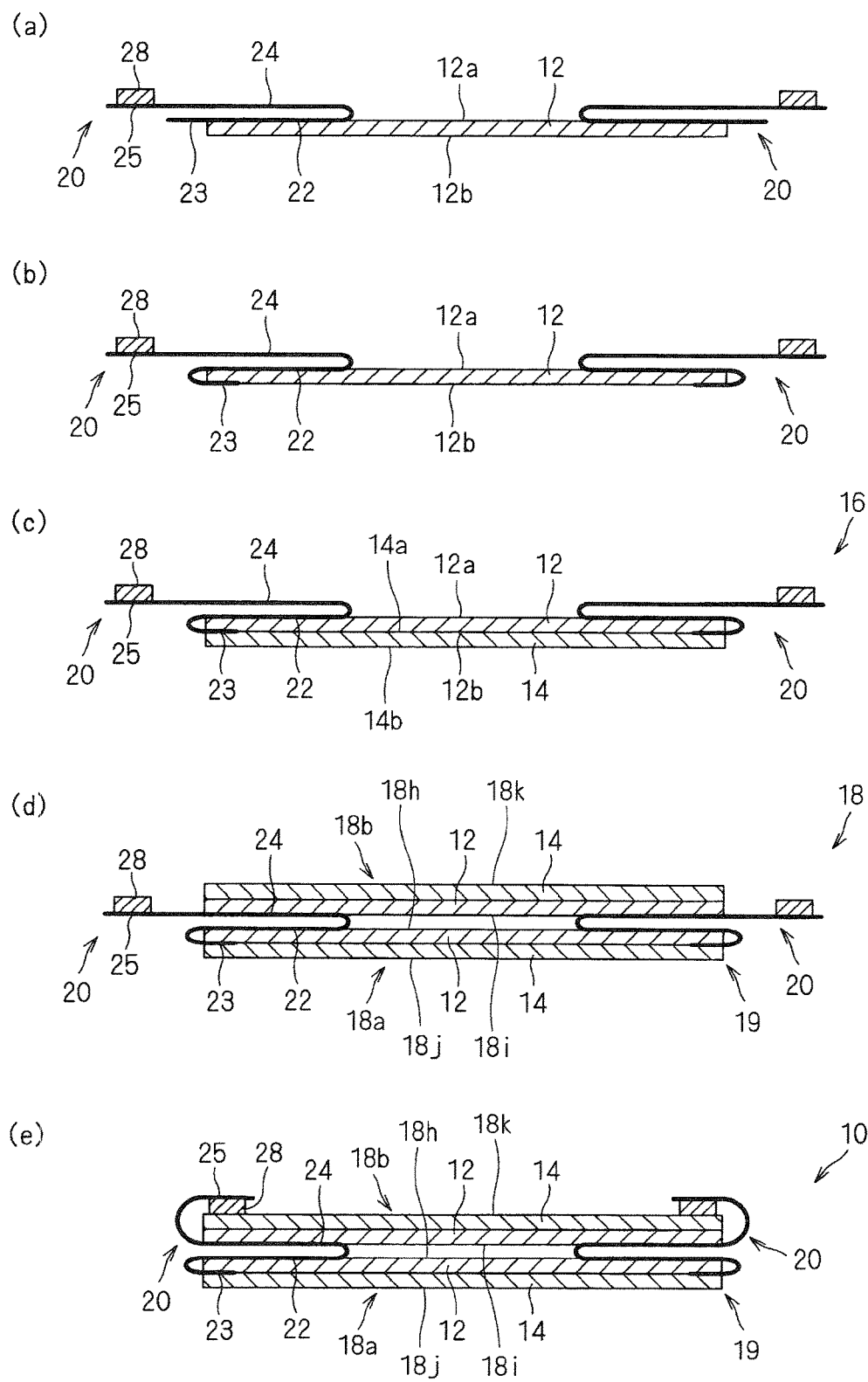
FIG. 2 Schematic views of cross sections in the production steps (first embodiment).

As schematically shown in FIG. 1 and FIG. 2, the disposable underwear-type diaper 10 is produced, briefly, by bonding a first continuous body 12 and a second continuous body 14 together to form a composite continuous body 16, cutting it into an individual piece 18 and then, folding the individual piece 18 in two. Hereinafter, the method for producing the disposable underwear-type diaper 10 will be described.

(1) As shown in FIG. 1(*a*) and FIG. 2(*a*), fasteners 20 are arranged in predetermined positions of one main surface 12*a* of the first continuous body 12.

The first continuous body 12 is a belt-like member having a pair of side edges 12*s* and 12*t* parallel to each other. The first continuous body 12 is conveyed in a direction parallel to the side edges 12*s* and 12*t* as shown by the arrow 12*x*.

The fastener 20 is a sheet-like member folded in two so that a first portion 22 and a second portion 24 are laid one over the other. The fasteners 20 are arranged at intervals along the pair of side edges 12*s* and 12*t* of the first continuous body 12 so that the main surface of the first portion 22 is in contact with the one main surface 12*a* of the first continuous body 12 and when viewed from the direction of the normal to the one main surface 12*a* of the first continuous body 12 (in FIG. 1, the direction vertical to the plane of the figure and in FIG. 2, the up-down direction of the plane of the figure), both ends 23 and 25 are disposed on the outside of the one main surface 12*a* of the first continuous body 12. A pair of fasteners 20 are arranged in the same position, in the conveyance direction 12*x*, of the first continuous body 12. The fastener 20 disposed along the one side edge 12*s* of the first continuous body 12 and the fastener 20 disposed along the other side edge 12*t* thereof are arranged on the one main surface 12*a* of the first continuous body 12 so as to face each other in a direction in which the side edges 12*s* and 12*t* face each other, that is, a direction 12*y* perpendicular to the conveyance direction 12*x*.

In the fastener 20, in order that the state where it is folded in two is maintained, an adhesive agent for temporary bonding may be provided between the first portion 22 and the second portion 24 facing each other, or the first portion 22 and the second portion 24 may be temporarily bonded by embossing.

The fasteners 20 are conveyed together with the first continuous body 12 while being held in a state of being arranged on the first continuous body 12. If necessary, in order that the positions of the fasteners 20 with respect to the first continuous body 12 are not shifted during the conveyance, the fasteners 20 are temporarily fixed with an adhesive agent or by embossing, the fasteners 20 are conveyed in a state of being pinned so as to be temporarily fixed to the first continuous body 12, or the fasteners 20 and the first continuous body 12 are sandwiched between belts or rollers so that they are conveyed in synchronism.

(2) Then, as shown in FIG. 1(*a*) and FIG. 2(*b*), the one end 23 of the fastener 20, that is, the end 23 of the first portion 22 disposed on the side of the first continuous body 12 is bent so as to be laid over the other main surface 12*b* of the first continuous body 12.

The one end 23 of the fastener 20 may be bent so as to be laid over the other main surface 12*b* of the first continuous body 12 when the fastener 20 is disposed on the one main surface 12*a* of the first continuous body 12 or therebefore.

(3) Then, as shown in FIG. 1(*a*) and FIG. 2(*c*), in a state where the one ends 23 of the fasteners 20 are bent so as to be laid over the other main surface 12*b* of the first continuous body 12, the belt-like second continuous body 14 is laid over the other main surface 12*b* of the first continuous body 12 while being conveyed as shown by the arrow 14*x*, and the one ends 23 of the fasteners 20 are sandwiched between the first continuous body 12 and the second continuous body 14. Then, the first continuous body 12 and the second continuous body 14 are bonded together and the one ends 23 of the fasteners 20 are fixed by bonding them to at least one of the first continuous body 12 and the second continuous body 14, thereby forming the composite continuous body 16. Although details will be described later, the composite continuous body 16 is formed so as to include an absorber 13.

The bonding of the first continuous body 12 and the second continuous body 14 and the bonding of the one end 23 of the fastener 20 and the first continuous body 12 and/or the second continuous body 14 may be performed in any order; these may be performed simultaneously or in tandem. As the bonding method, an adhesive agent, thermal fusion bonding, ultrasonic bonding or the like is selected as appropriate.

(4) Then, the composite continuous body 16 is cut in the direction 12*y* perpendicular to the pair of side edges 12*s* and 12*t* of the first continuous body 12 as shown by the chain line 17 in FIG. 1(*a*), thereby forming the individual piece 18 including a pair of fasteners 20 as shown in FIG. 1(*b*). As shown in FIG. 1(*b*), the pair of fasteners 20 are included in one region 18a (first region 18a) of the individual piece 18 divided in two by an imaginary line 18x, and are not included in the other region 18b (second region 18b). The imaginary line 18x dividing the individual piece 18 in two extends between end edges 18p and 18q of the individual piece 18 formed by cutting the composite continuous body 16 parallel to the end edges 18p and 18q.

On side edges 18y and 18z, concave portions 18s and 18t are formed in the vicinity of the intersections with the imaginary line 18x. For example, the pair of concave portions 18s and 18t may be formed by removing the parts corresponding to the concave portions 18s and 18t by cutting them simultaneously, in advance or subsequently when the composite continuous body 16 is cut in the perpendicular direction 12y. The pair of concave portions 18s and 18t may be formed by bonding the first continuous body 12 and the second continuous body 14 together after removing the parts corresponding to the concave portions 18s and 18t by cutting them for each of the first continuous body 12 and the second continuous body 14.

The individual piece 18 is formed so that the first continuous body 12 and the second continuous body 14 are bonded together at least along the end edges 18p and 18q and the side edges 18y and 18z extending between the end edges 18p and 18q.

(5) Then, as shown in FIG. 1(c) and FIG. 2(d), the individual piece 18 is folded in two along the imaginary line 18x so that the fasteners 20 are sandwiched between the first region 18a and the second region 18b. Inner main surfaces 18h and 18i, facing each other, of the first region 18a and the second region 18b are formed of the first continuous body 12, and outer main surfaces 18j and 18k on the opposite side of the inner main surfaces 18h and 18i are formed of the second continuous body 14.

(6) Then, as shown in FIG. 1(d) and FIG. 2(e), the end 25 (that is, the other end 25) of the second portion 24 of the fastener 20 is bent to the side opposite to the one end 23 of the fastener 20, and the other end 25 of the fastener 20 is fixed to the second region 18b of the individual piece 18.

FIG. 1 and FIG. 2 illustrate a case where the other end 25 is detachably fixed to the second region 18b through a hook and loop fastener 28 previously fixed to the other end 25 of the fastener 20. The outer main surface 18k to which the hook and loop fastener 28 is fixed is made of, for example, nonwoven cloth.

Figure 5:
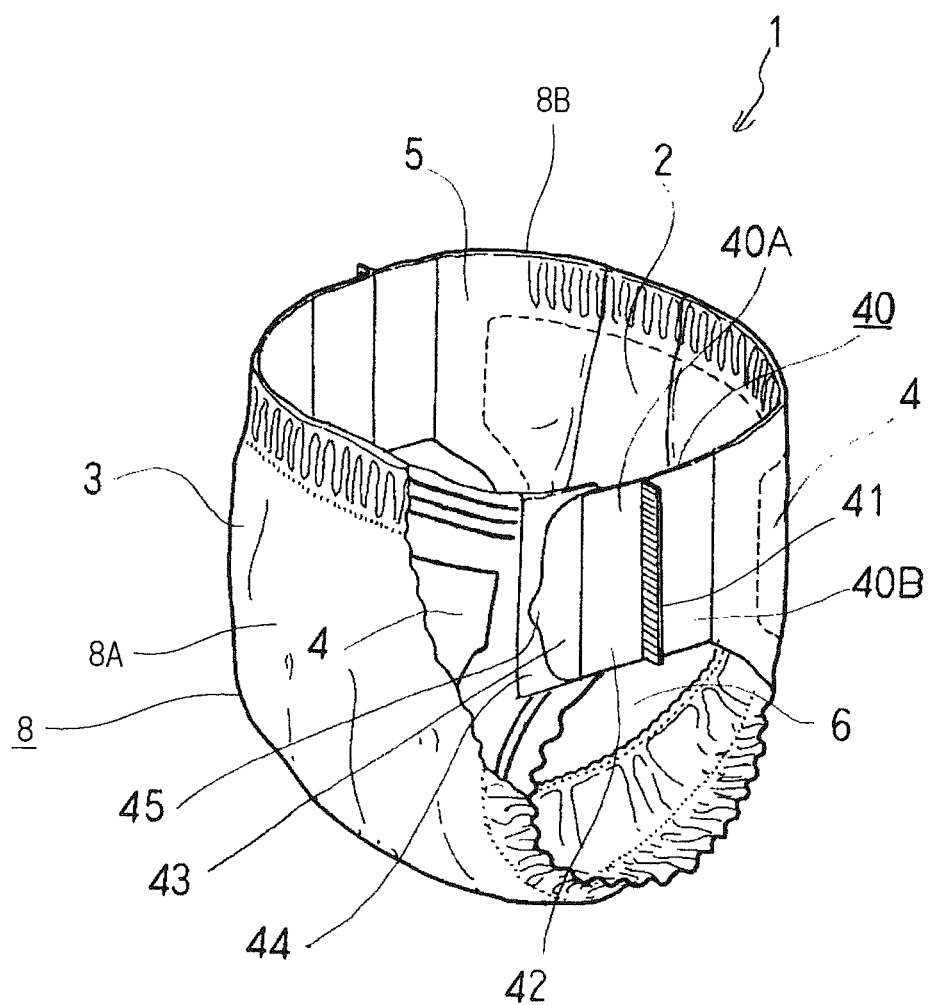
FIG. 5 A partially broken perspective view of a disposable underwear-type diaper (first conventional example).
Figure 6:
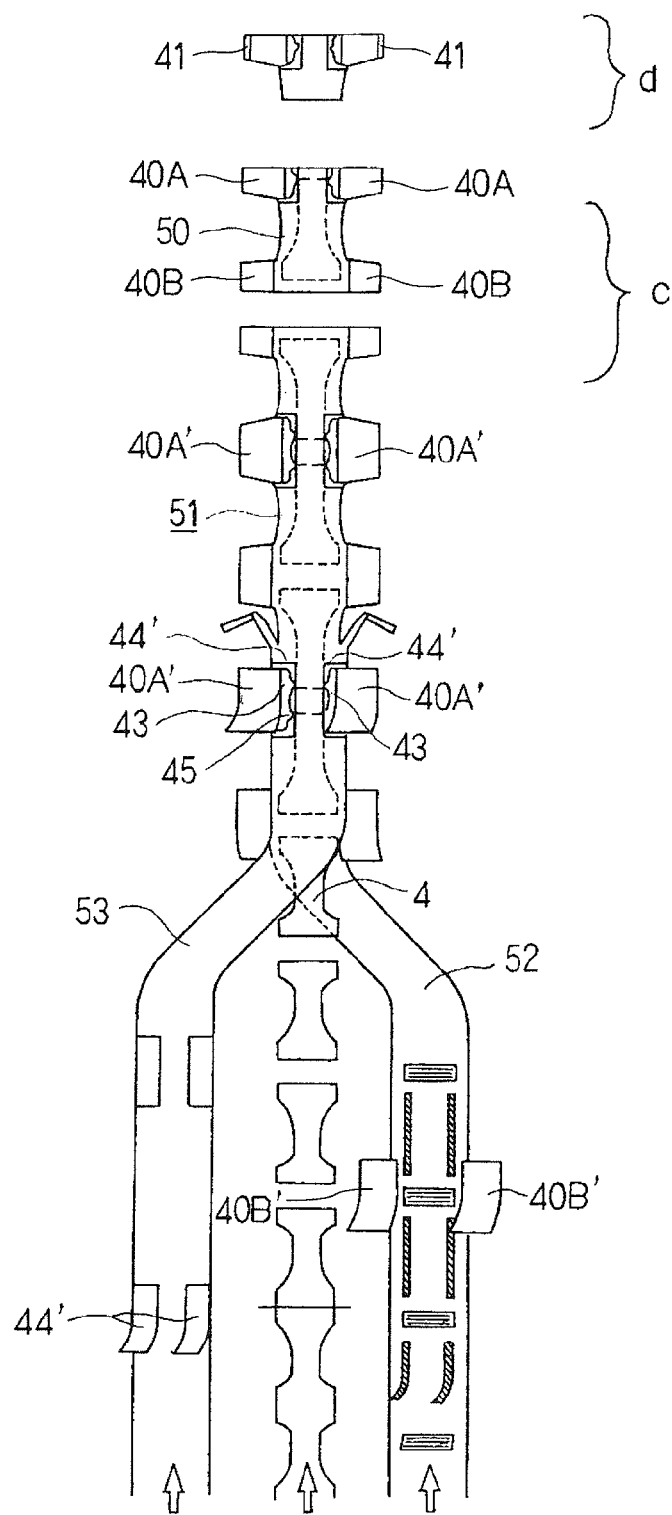
FIG. 6 A schematic view of production steps of the disposable underwear-type diaper (first conventional example).

Not only by this method but the other end 25 may be fixed to the second region 18b by welding, thermal fusion bonding and other appropriate methods. The other end 25 may be detachably fixed to the second region 18b by using a tape portion and a target zone as shown in FIG. 5 and FIG. 6.

In the individual piece 18 folded in two, a middle portion between the one end 23 and the other end 25 of the fastener 20 is sandwiched between the first region 18a and the second region 18b. Consequently, the handling of the individual piece 18 thereafter is easy compared with a case where the middle portion of the fastener 20 is disposed on the outside of the individual piece 18 as in a second embodiment described later.

The other end 25 of the fastener 20 may be bent halfway before the overlaying of the first region 18a and the second region 18b of the individual piece 18 is completed. In that case, after the overlaying of the first region 18a and the second region 18b of the individual piece 18 is completed, the other end 25 of the fastener 20 is completely bent and laid over the second region 18b, and the other end 25 of the fastener 20 is fixed to the second region 18b.

By the above-described steps of (1) to (6), the disposable underwear-type diapers 10 can be continuously produced while the first continuous body 12 and the second continuous body 14 are being conveyed.

The produced disposable underwear-type diaper 10 is provided with a body 19 including an inner member formed of the first continuous body 12 and an outer member formed of the second continuous body 14, and the fasteners 20. The body 19 has the pair of end edges 18p and 18q facing each other and the pair of side edges 18y and 18z extending between the end edges 18p and 18q and facing each other. The body 19 is divided into two parts of the first region 18a and the second region 18b by the imaginary line 18x. The one end 23 of the fastener 20 is fixed to the body 19 in a state of being disposed between the first continuous body 12 and the second continuous body 14, that is, between the inner member and the outer member. The other end 25 of the fastener 20 is fixed to the outer main surface 18k of the second region 18b of the body 19.

When the first region 18a and the second region 18b of the body 19 are separated from each other to increase the space between the first region 18a and the second region 18b, a waist opening is formed between the pair of end edges 18p and 18q of the body 19. Moreover, between a pair of fasteners 20 and the imaginary line 18x (bend line), a pair of leg openings are formed along the concave portions 18s and 18t formed on the side edges 18y and 18z of the body 19.

The body 19 includes a liquid transmitting top sheet, a liquid non-transmitting back sheet and the absorber 13 disposed between the top sheet and the back sheet, and the inner main surfaces 18h and 18i of the first region 18a and the second region 18b of the body 19 are formed of the top sheet. The outer main surfaces 18j and 18k of the first region 18a and the second region 18b of the body 19 may be formed of the back sheet. Alternatively, the body 19 may further include a liquid transmitting or liquid non-transmitting cover sheet so that the outer main surfaces 18j and 18k of the first region 18a and the second region 18b of the body 19 are formed of the cover sheet.

Although not shown, an elastic member for providing elasticity may be provided along the waist opening and the leg openings, and three-dimensional gathers standing at the wearer's crotch and in close contact with the skin may be formed on the top sheet.

Since it is unnecessary to form a seam in the middle portion between the one end 23 and the other end 25 of the fastener 20, the seam can be eliminated from the middle portion so that a sense of discomfort by the seam is not given to the wearer. That is, the fastener 20 can be formed so that the softness and texture of the middle portion are uniform. For example, the fastener 20 is formed so that at least one or more than one member is continuous in the middle portion.

The first continuous body 12 and the second continuous body 14 can be made in various modes as follows:

In a first mode, the first continuous body 12 includes a top sheet continuous body which is a belt-like sheet member for forming a liquid transmitting top sheet. The one main surface 12a of the first continuous body 12, that is, the inner main surfaces 18h and 18i of the first region 18a and the second region 18b are formed of the top sheet continuous body. The second continuous body 14 includes a back sheet continuous body which is a belt-like sheet member for forming a liquid non-transmitting back sheet. The first continuous body 12 and the second continuous body 14 are bonded together in a state where the absorber 13 is disposed between the first continuous body 12 and the second continuous body 14.

The absorber 13 may be disposed between the first continuous body 12 and the second continuous body 14 immediately before the first continuous body 12 and the second continuous body 14 are bonded together. Or it may be performed to dispose the absorber 13 on the side of the other main surface 12b of the first continuous body 12 simultaneously with, or before or after the step of arranging the fasteners 20 on the one main surface 12a of the first continuous body 12 and then, bond the first continuous body 12 and the second continuous body 14 together. Or it may be performed to dispose the absorber 13 on the second continuous body 14 and then, bond the first continuous body 12 and the second continuous body 14 together.

In a second mode, the first continuous body 12 includes a liquid transmitting top sheet continuous body forming the one main surface 12a of the first continuous body 12, a liquid non-transmitting back sheet continuous body forming the other main surface 12b of the first continuous body 12, and the absorber 13 disposed between the top sheet continuous body and the back sheet continuous body. The second continuous body 14 includes a cover sheet continuous body which is a belt-like sheet member for forming a liquid transmitting or liquid non-transmitting cover sheet. In this case, when the fasteners 20 are arranged on the one main surface of the first continuous body 12, the absorber 13 is already disposed on the first continuous body 12.

In a third mode, the first continuous body 12 includes a top sheet continuous body. The one main surface 12a of the first continuous body 12 is formed of the top sheet continuous body. The second continuous body 14 includes a liquid non-transmitting back sheet continuous body and a liquid transmitting or liquid non-transmitting cover sheet continuous body. Of the main surfaces 14a and 14b of the second continuous body 14, the main surface 14a on the side of the first continuous body 12 is formed of the back sheet continuous body. The first continuous body 12 and the second continuous body 14 are bonded together in a state where the absorber 13 is disposed between the first continuous body 12 and the second continuous body 14.

Second Embodiment

The second embodiment will be described with reference to FIG. 3 and FIG. 4. In the following, differences from the first embodiment will be mainly described, and the same parts as those of the first embodiment are denoted by the same reference designations.

FIGS. 3(a) and 3(b) are plan views schematically showing production steps. FIG. 4(a) is a schematic view of a cross section taken along line S-S of FIG. 3(a). FIG. 4(b) is a schematic view of a cross section taken along line T-T of FIG. 3(b).

As in the first embodiment, the first continuous body 12 and the second continuous body 14 are bonded together to form the composite continuous body 16, and the composite continuous body 16 is cut to form the individual piece 18 divided into two parts of the first region 18a and the second region 18b by the imaginary line 18x.

Then, as shown in FIG. 3(a) and FIG. 4(a), the individual piece 18 is folded in two along the imaginary line 18x to the side opposite to that in the first embodiment. In the individual piece 18 folded in two, inner main surfaces 18m and 18n, facing each other, of the first region 18a and the second region 18b are formed of the second continuous body 14, and outer main surfaces 18u and 18v on the opposite side of the inner main surfaces 18m and 18n are formed of the first continuous body 12. The middle portion between the one end 23 and the other end 25 of the fastener 20 is disposed on the outer main surface 18u of the first region 18a of the individual piece 18.

Then, as shown in FIGS. 4(a) and 4(b), the other end 25 of the fastener 20 is bent to the same side as the one end 23, and fixed to the second region 18b of the individual piece 18. When fixing is performed by using the hook and loop fastener 28, the hook and loop fastener 28 is provided on the side opposite to that in the first embodiment at the other end 25 of the fastener 20.

By the above-described steps, disposable underwear-type diapers 10a can be continuously produced while the first continuous body 12 and the second continuous body 14 are being conveyed.

The produced disposable underwear-type diaper 10a is provided with a body 19 including an inner member formed of the second continuous body 14 and an outer member formed of the first continuous body 12, and the fasteners 20. As in the first embodiment, the body 19 has the pair of end edges 18p and 18q facing each other and the pair of side edges 18y and 18z extending between the end edges 18p and 18q and facing each other. The body 19 is divided into two parts of the first region 18a and the second region 18b by the imaginary line 18x. The one end 23 of the fastener 20 is fixed to the body 19 in a state of being disposed between the first continuous body 12 and the second continuous body 14, that is, between the inner member and the outer member. The other end 25 of the fastener 20 is fixed to the outer main surface 18v of the second region 18b of the body 19.

When the first region 18a and the second region 18b of the body 19 are separated from each other to increase the space between the first region 18a and the second region 18b, a waist opening is formed between the pair of end edges 18p and 18q of the body 19. Moreover, between a pair of fasteners 20 and the imaginary line 18x, a pair of leg openings are formed along the concave portions 18s and 18t formed on the side edges 18y and 18z of the body.

Since it is unnecessary to form a seam in the middle portion between the one end 23 and the other end 25 of the fastener 20, the seam can be eliminated from the middle portion so that a sense of discomfort by the seam is not given to the wearer. That is, the fastener 20 can be formed so that the softness and texture of the middle portion are uniform. For example, the fastener 20 is formed so that at least one or more than one member is continuous in the middle portion.

The first continuous body 12 and the second continuous body 14 can be made in various modes as follows:

In a first mode, the first continuous body 12 includes a back sheet continuous body which is a belt-like sheet member for forming a liquid non-transmitting back sheet. The second continuous body 14 includes a top sheet continuous body which is a belt-like sheet member for forming a liquid transmitting top sheet. Of the main surfaces 14a and 14b of the second continuous body 14, the main surface 14b on the opposite side of the first continuous body 12, that is, the inner main surfaces 18m and 18n of the first region 18a and the second region 18b are formed of the top sheet continuous body. The first continuous body 12 and the second continuous body 14 are bonded together in a state where the absorber 13 is disposed between the first continuous body 12 and the second continuous body 14.

In a second mode, the first continuous body 12 includes a cover sheet continuous body which is a liquid transmitting or liquid non-transmitting belt-like sheet member for forming a cover sheet, and a back sheet continuous body. Of the main surfaces 12a and 12b of the first continuous body 12, the main surface 12b on the side of the second continuous body 14 is formed of the back sheet continuous body. The second continuous body 14 includes a liquid transmitting top sheet continuous body. Of the main surfaces 14a and 14b of the second continuous body 14, the main surface 14b on the opposite side of the first continuous body 12 is formed of the top sheet continuous body. The first continuous body 12 and the second continuous body 14 are bonded together in a state where the absorber 13 is disposed between the first continuous body 12 and the second continuous body 14.

In a third mode, the first continuous body 12 includes a liquid transmitting or liquid non-transmitting cover sheet continuous body. The second continuous body 14 includes a top sheet continuous body, a back sheet continuous body, and the absorber 13 disposed between the top sheet continuous body and the back sheet continuous body. Of the main surfaces 14a and 14b of the second continuous body 14, the main surface 14b on the opposite side of the first continuous body 12 is formed of the top sheet continuous body. In this case, when the fasteners 20 are arranged on the one main surface of the first continuous body 12, the absorber 13 is already disposed on the first continuous body 12.

<Summary> As described above, the disposable underwear-type diapers 10 and 10a provided with the fastener 20 having no seam in the middle portion can be continuously produced by using the fastener 20 folded in two.

The present invention is not limited to the above embodiments but may be carried out with various changes being added thereto.

DESCRIPTION OF REFERENCE DESIGNATIONS 10, 10a Disposable underwear-type diaper
12 First continuous body (inner member; outer member)
12a One main surface
12b The other main surface
12s, 12t Side edge
12x Conveyance direction
12y Perpendicular direction
13 Absorber
14 Second continuous body (outer member; inner member)
14a, 14b Main surface
16 Composite continuous body
18 Individual piece
18a First region
18b Second region
18h, 18i Inner main surface
18j, 18k Outer main surface
18m, 18n Inner main surface
18p, 18q End edge
18s, 18t Concave portion
18u, 18t Outer main surface
18x Imaginary line
18y, 18z Side edge
19 Body
20 Fastener
22 First portion
23 End (one end)
24 Second portion
25 End (the other end)
28 Hook and loop fastener

The invention claimed is:

1. A method for producing a disposable underwear-type diaper comprising:
a first step of arranging sheet-like fasteners folded in two, on one main surface of a belt-like first continuous body having a pair of side edges, at intervals along the pair of side edges of the first continuous body so that a main surface of each of the fasteners is in contact with the one main surface, that two ends of the fasteners are disposed on an outside of the one main surface of the first continuous body when viewed from a direction normal to the one main surface and that a pair of the fasteners faces each other in a direction in which the side edges of the first continuous body face each other;
a second step of forming a composite continuous body by bending each end, on the first continuous body side, of the fasteners so as to be laid over another main surface of the first continuous body, then laying a belt-like second continuous body over the another main surface of the first continuous body, and then bonding the first continuous body and the second continuous body together so that the each end of the fasteners is fixed by bonding the each end of the fasteners to at least one of the first continuous body and the second continuous body;
a third step of cutting the composite continuous body to thereby form an individual piece divided by an imaginary line in two parts of a first region including the pair of fasteners facing each other and a second region not including the fasteners; and
a fourth step of folding the individual piece in two along the imaginary line so that the first region and the second region are laid one over the other, bending other ends of the fasteners so as to be laid over the second region, and then, fixing the other ends to the second region,
wherein in the fourth step, after the individual piece is folded in two along the imaginary line so that the fasteners are sandwiched between the first region and the second region, each of the other ends of the fasteners is bent to a side opposite to the each of the ends and laid over the second region, and the other ends are fixed to the second region,
the first continuous body includes a liquid transmitting top sheet forming the one main surface of the first continuous body, a liquid non-transmitting back sheet forming the other main surface of the first continuous body, and an absorber disposed between the top sheet and the back sheet, and
the second continuous body includes a liquid transmitting or liquid non-transmitting cover sheet.

* * * * *